(12) United States Patent
    Koizumi et al.

(10) Patent No.: US 10,995,065 B2
(45) Date of Patent: May 4, 2021

(54) METHOD FOR PRODUCING PURIFIED METHIONINE AND METHOD FOR PREVENTING CAKING OF METHIONINE

(71) Applicant: SUMITOMO CHEMICAL COMPANY, LIMITED, Tokyo (JP)

(72) Inventors: Yoshiyuki Koizumi, Niihama (JP); Naoya Yamashiro, Niihama (JP); Akira Morimoto, Niihama (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/631,328

(22) PCT Filed: Jul. 19, 2018

(86) PCT No.: PCT/JP2018/027014
§ 371 (c)(1),
(2) Date: Jan. 15, 2020

(87) PCT Pub. No.: WO2019/017415
PCT Pub. Date: Jan. 24, 2019

(65) Prior Publication Data
US 2020/0207708 A1    Jul. 2, 2020

(30) Foreign Application Priority Data

Jul. 19, 2017    (JP) .............................. JP2017-140093

(51) Int. Cl.
    *C07C 319/28*    (2006.01)
    *C07C 323/58*    (2006.01)
(52) U.S. Cl.
    CPC .......... *C07C 319/28* (2013.01); *C07C 323/58* (2013.01)

(58) Field of Classification Search
    CPC ........................... C07C 319/28; C07C 323/58
    See application file for complete search history.

(56) References Cited

U.S. PATENT DOCUMENTS

| 2,443,391 A | 6/1948 | Kirkpatrick et al. |
| 3,931,307 A * | 1/1976 | Eikelmann ............ C07C 227/40 562/554 |
| 5,463,120 A | 10/1995 | Giraud et al. |

FOREIGN PATENT DOCUMENTS

| CN | 106432020 A | 2/2017 |
| EP | 2 186 798 A1 | 5/2010 |

(Continued)

OTHER PUBLICATIONS

English translation of the International Search Report, dated Aug. 21, 2018, for International Application No. PCT/JP2018/027014.

(Continued)

*Primary Examiner* — Yate' K Cutliff
(74) *Attorney, Agent, or Firm* — Birch, Stewart, Kolasch & Birch, LLP

(57) ABSTRACT

The present invention addresses the problem of providing a method for producing purified methionine, the method being capable of preventing the caking of methionine. The present invention pertains to a method for producing purified methionine from crude methionine, the method comprising (1) a step for obtaining a wet cake of washed crude methionine, (2) a step for adjusting the pH of the wet cake, and (3) a step for drying the wet cake after the pH adjustment, wherein the pH of the wet cake after the pH adjustment is 5.2-6.1.

4 Claims, 2 Drawing Sheets

(56) References Cited

FOREIGN PATENT DOCUMENTS

| EP | 2821396 A1 | 1/2015 | | |
|----|----|----|----|----|
| EP | 3318552 A1 | 5/2018 | | |
| JP | 49-86320 A | 8/1974 | | |
| JP | 7-70051 A | 3/1995 | | |
| JP | 200-143617 A | * | 5/2000 | ........... C07C 319/20 |
| JP | 2000-143617 A | | 5/2000 | |
| JP | 2006-70024 A | | 3/2006 | |
| JP | 2007-63141 A | | 3/2007 | |
| WO | WO 2013-129405 A1 | | 9/2013 | |
| WO | WO 2017-000867 A1 | | 1/2017 | |

OTHER PUBLICATIONS

International Prelminary Report on Patentability and English Translation of the Written Opinion of the International Searching Authority, dated Jan. 21, 2020, for International Application No. PCT/JP2018/027014.

Singaporean Office Action for Singaporean Application No. 11202001471, dated Aug. 3, 2020.

Chinese Notification of the First Office Action and Search Report (including an English translation thereof) issued in corresponding Chinese Patent Application No. 201880038785.8 dated Dec. 21, 2020.

European Patent Office Communication and extended search report issued in the corresponding European Patent Application No. 18834474.1 dated Mar. 11, 2021.

* cited by examiner

METHOD FOR PRODUCING PURIFIED METHIONINE AND METHOD FOR PREVENTING CAKING OF METHIONINE

TECHNICAL FIELD

This patent application claims priority under the Paris Convention based on Japanese Patent Application No. 2017-140093 (filed Jul. 19, 2017) incorporated herein by reference in its entirety.

The present invention relates to a method for producing purified methionine and a method for preventing caking of methionine.

BACKGROUND ART

Methionine is obtained by a hydrolysis reaction of 5-(2-(methylthio)ethyl)imidazolidine-2,4-dione as shown in the following reaction formula (1), for example.

[Chemical 1]

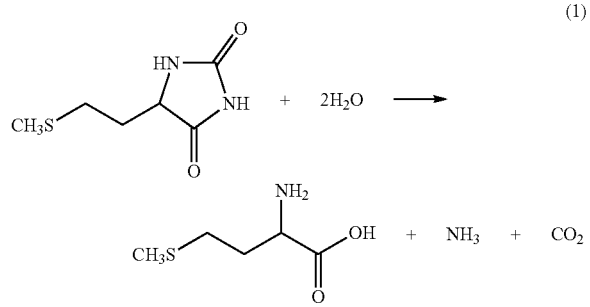

(1)

Methionine is useful as an animal feed additive. From the viewpoint of quality improvement, production cost reduction, etc., various studies have been conducted on a method for producing methionine (e.g., Patent Documents 1 and 2).

PRIOR ART DOCUMENTS

Patent Documents

Patent Document 1: Japanese Laid-Open Patent Publication No. 2000-143617
Patent Document 2: Japanese Laid-Open Patent Publication No. 2007-063141

SUMMARY OF THE INVENTION

Problem to be Solved by the Invention

Methionine has a powder form as a product. However, methionine may form cake during storage, and if such caking is promoted, lumps of methionine are formed. If lumps of methionine are contained in powdered methionine, handleability of methionine as a product may be impaired. Therefore, it is demanded to establish a technique capable of preventing caking of methionine so as not to form lumps of methionine.

In Patent Document 1, an object is to provide a method for producing easy-to-handle methionine having a large bulk specific gravity, and a technique for drying a methionine wet cake under mechanical stirring is studied. However, Patent Document 1 does not disclose any technique for preventing caking of methionine.

In Patent Document 2, a technique for producing methionine advantageously in terms of cost and wastewater treatment is studied. However, Patent Document 2 does not disclose any technique for preventing caking of methionine.

As descried above, although methionine is continuously produced for a long time, the prevention of caking of methionine is not sufficiently studied.

The present invention was conceived in view of the situations, and an object thereof is to provide a method for producing purified methionine capable of preventing caking of methionine and a method for preventing caking of methionine.

Means for Solving Problem

The present inventors intensively studied a technique capable of preventing caking of methionine and found that pH of methionine to be subjected to a drying treatment, i.e., a methionine wet cake, is related to caking of methionine, thereby completing the present invention. Therefore, a method for producing purified methionine according to the present invention is a method for producing purified methionine from crude methionine, the method comprising the steps of:
(1) obtaining a crude methionine wet cake washed with water;
(2) adjusting the pH of the wet cake; and
(3) drying the wet cake after pH adjustment, wherein
the pH of the wet cake after pH adjustment is 5.2 or more and 6.1 or less.

In this method for producing purified methionine, the wet cake adjusted to a specific pH is subjected to a drying treatment based on the knowledge about the prevention of caking of methionine described above. In the purified methionine obtained by this production method, caking is effectively prevented. As a result, the formation of lump methionine is suppressed, so that this purified methionine is extremely favorable in handleability.

In this method for producing purified methionine, the pH of the wet cake after pH adjustment is preferably 5.7 or more. According to this embodiment, the caking of the purified methionine can more effectively be prevented.

Furthermore, a method for preventing caking of methionine according to the present invention is a method for preventing caking of methionine, the method comprising the steps of:
(1) obtaining a methionine wet cake;
(2) adjusting the pH of the wet cake; and
(3) drying the wet cake after pH adjustment, wherein
the pH of the wet cake after pH adjustment is 5.2 or more and 6.1 or less.

Also in this method for preventing caking of methionine, the wet cake adjusted to a specific pH is subjected to a drying treatment. Therefore, in methionine to which this method for preventing caking of methionine is applied, caking is effectively prevented. As a result, the formation of lump methionine is suppressed, so that this methionine is extremely favorable in handleability.

In this method for preventing caking of methionine, the pH of the wet cake after pH adjustment is preferably 5.7 or more. According to this embodiment, the caking of the methionine can more effectively be prevented.

Effect of the Invention

The production method of the present invention provides purified methionine prevented from caking. The application of the caking prevention method of the present invention prevents caking of methionine. Therefore, the present invention provides the method for producing purified methionine capable of effectively preventing caking of methionine and the method for preventing caking of methionine.

MODES FOR CARRYING OUT THE INVENTION

The present invention will now be described in detail based on preferred embodiments with appropriate reference to the drawings.

[Method for Producing Purified Methionine]

Figure 1:
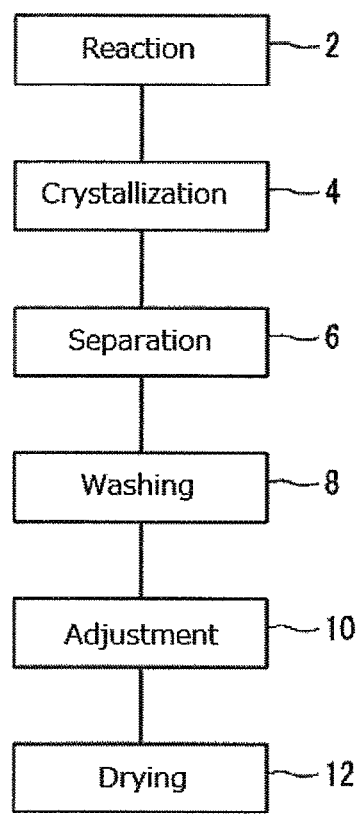
FIG. 1 is a flowchart showing a flow of steps comprised in a method for producing purified methionine according to an embodiment of the present invention.

FIG. 1 shows a flow of steps comprised in a method for producing purified methionine according to an embodiment of the present invention. This production method comprises a reaction step 2, a crystallization step 4, a separation step 6, a water washing step 8, an adjustment step 10, and a drying step 12. Details of the steps will hereinafter be described.

In an embodiment of the present invention, a water-washed crude methionine wet cake described later may be obtained by a series of steps from the reaction step 2 to the water washing step 8, and each of the reaction step 2, the crystallization step 4, and the separation step 6 is not particularly limited. In this production method, each of the reaction step 2, the crystallization step 4, the separation step 6, and the water washing step 8 may be configured to have the same details as those of the step in a conventionally known production method.

(Reaction Step 2)

At the reaction step 2, 5-[2-(methylthio)ethyl]imidazolidine-2,4-dione is used as a raw material and is hydrolyzed in the presence of an alkali compound such as potassium hydroxide, sodium hydroxide, potassium carbonate, potassium hydrogencarbonate, etc. As a result, a reaction liquid containing methionine as an alkali salt is obtained.

At this reaction step 2, an amount of the alkali compound used is usually 2 to 10 mol, preferably 3 to 6 mol in terms of potassium or sodium per 1 mol of 5-[2-(methylthio)ethyl]imidazolidine-2,4-dione. An amount of water used is usually set to have the mass 2 to 20 times the mass of 5-[2-(methylthio)ethyl]imidazolidine-2,4-dione. The hydrolysis is usually performed in a reaction vessel (not shown) with a gauge pressure set to 0.5 to 1 MPa and a temperature set to 150 to 200° C. A reaction time is usually set in a range of 10 minutes to 24 hours.

(Crystallization Step 4)

At the crystallization step 4, carbon dioxide is introduced into the reaction liquid obtained at the reaction step 2. By introducing carbon dioxide, methionine is released from the alkali salt of methionine, and methionine is precipitated in the reaction liquid. As a result, a slurry containing methionine as a solid component is obtained.

At this crystallization step 4, carbon dioxide is supplied to the reaction vessel containing the reaction liquid. By supplying the carbon dioxide, the gauge pressure in the reaction vessel is adjusted to usually 0.1 to 1 MPa, preferably 0.2 to 0.5 MPa. The temperature in the reaction vessel (also referred to as crystallization temperature) is usually set to 0 to 50° C., preferably 10 to 30° C. A time required for crystallization (also referred to as crystallization time) is basically a time until carbon dioxide is saturated in the reaction liquid so that methionine is sufficiently precipitated and is usually 30 minutes to 24 hours.

(Separation Step 6)

Figure 2:
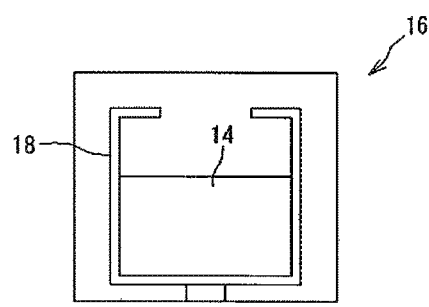
FIG. 2 is a schematic view showing a state in which a slurry is put into an apparatus for solid-liquid separation.
Figure 3:
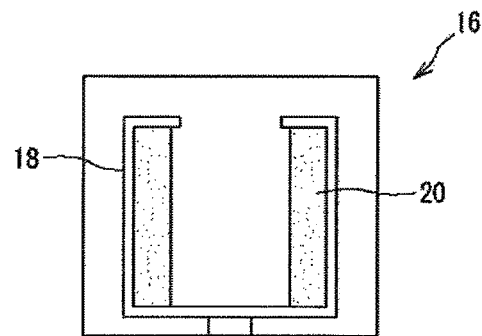
FIG. 3 is a schematic view showing a step of forming a wet cake in the embodiment of the present invention.

At the separation step 6, as shown in FIG. 2, the slurry 14 obtained at the crystallization step 4 is put into a basket 18 of a centrifuge 16. After the slurry is put in, the basket 18 is rotated and the slurry 14 is separated into solid and liquid. As a result, as shown in FIG. 3, the solid component in the slurry 14 forms a mass (wet cake) 20 captured by the basket 18. The liquid component in the slurry 14 is recovered as a filtrate.

The slurry 14 contains impurities such as the alkali compound used for hydrolysis, a dimer of methionine, and glycine and alanine generated by decomposition of methionine. Therefore, the mass 20 captured in the basket 18 contains these impurities in addition to methionine. In the present invention, methionine coexistent with impurities is crude methionine. Therefore, the slurry 14 obtained at the reaction step 2 described above is a crude methionine slurry, and the mass 20 described above captured in the basket 18 is a crude methionine wet cake. Therefore, at the separation step 6, the crude methionine slurry 14 is separated into solid and liquid, and the crude methionine wet cake 20 is obtained.

In the present invention, the solid-liquid separation of the slurry 14 is not limited to the centrifugal separation method. Preferably, various conditions for the solid-liquid separation are suitably set so that the water content of the wet cake 20 is 40 mass % or less.

(Washing Step 8)

At the washing step 8, the wet cake 20 obtained at the separation step 6 is washed with washing water. Although not shown, at this washing step 8, the washing water is sprayed to the wet cake 20 by using a spray. As a result, the entire wet cake 20 is washed with water, and the impurities described above are removed from the wet cake 20. In the present invention, the wet cake 20 after removal of the impurities is a crude methionine wet cake 20$w$ washed with water (also referred to as a water-washed wet cake 20$w$). Therefore, at this water washing step 8, the crude methionine wet cake 20$w$ washed with water is obtained. At this washing step 8, the temperature of the washing water is appropriately set usually in a range of 5 to 35° C.

In the present invention, the crude methionine after removal of impurities is also referred to as clean methionine. Therefore, the crude methionine wet cake 20$w$ washed with water described above is a clean methionine wet cake.

In the present invention, a state of the crude methionine wet cake 20 after removal of impurities means a state in which a ratio of total parts by mass of impurities to 100 parts by mass of methionine in the wet cake 20 after washing with water, i.e., the water-washed wet cake 20$w$, is 50% or less of a ratio of total parts by mass of impurities to 100 parts by mass of methionine in the wet cake 20 before washing.

As described above, when the crude methionine slurry 14 is subjected to solid-liquid separation, the wet cake 20 is obtained. The wet cake obtained by further washing the wet cake 20 with water is the crude methionine wet cake 20$w$ washed with water. In the present invention, the wet cake obtained by solid-liquid separation of the methionine slurry obtained by adding washing water to the crude methionine slurry 14 is also the crude methionine wet cake 20w washed with water.

At this washing step 8, from the viewpoint of sufficiently removing impurities, the mass of the washing water sprayed to the crude methionine wet cake 20 is preferably 100 g or more, and preferably 300 g or less, relative to the mass of 100 g of the wet cake 20. The mass of the washing water is more preferably 150 g or more, and more preferably 250 g or less, relative to the mass of 100 g of the wet cake 20.

For the washing water, water may be used, or an aqueous solution containing methionine may be used. From the viewpoint of preventing methionine contained in the wet cake 20 from being dissolved in the washing water and improving a yield of methionine as a product, the washing water is preferably an aqueous solution containing methionine. In this case, the concentration of methionine contained in the washing water is preferably 1.0 mass % or more, more preferably 2.0 mass % or more. Since the saturated solubility of methionine in water at ordinary temperature and normal pressure is 3.0 mass %, the upper limit of the concentration of methionine in the washing water is 3.0 mass %. Therefore, the concentration of methionine contained in the washing water is 3.0 mass % or less.

The water used in the present invention is not particularly limited. Examples of the water comprise distilled water, pure water, ion exchange water, and condensed water of water vapor.

(Adjustment Step 10)

At the adjustment step 10, the pH of the crude methionine wet cake 20w washed with water described above is adjusted by using a pH-adjustment water. In the present invention, the wet cake 20w adjusted in pH with the pH-adjustment water is a wet cake 20p after pH adjustment (also referred to as an adjusted wet cake 20p).

Although not shown, at the adjustment step 10, it is preferable that the pH-adjustment water is sprayed by using a spray toward the water-washed wet cake 20w captured in the basket 18 of the centrifuge 16 to adjust the pH of this wet cake 20w. The temperature of the pH-adjustment water is appropriately set usually in a range of 5 to 35° C.

At the adjustment step 10, the pH of the entire wet cake 20w may be adjusted, and no particular limitation is placed on a method for adjusting the pH, for example, how the pH-adjustment water is sprayed to the wet cake 20w.

The pH-adjustment water may be sprayed to the water-washed wet cake 20w at any time before the drying step 12 described later. In the production of methionine, the wet cake obtained by solid-liquid separation is usually put into a dryer via a hopper (not shown). Therefore, after the wet cake 20w is taken out from the basket 18 and the wet cake 20w is put into the hopper, the pH-adjustment water may be sprayed to the wet cake 20w in the hopper to adjust the pH of the wet cake 20w. The pH-adjustment water may be sprayed to the wet cake 20w to adjust the pH of the wet cake 20w before the wet cake 20w in the hopper is put into the dryer. The timing of adjustment of the pH of the wet cake 20w is appropriately determined in consideration of the productivity of methionine.

Furthermore, in the present invention, for example, the clean methionine wet cake 20w may be put into the pH-adjustment water to obtain a clean methionine slurry, and this slurry may be separated into solid and liquid as in the separation step 6 described above to obtain the wet cake 20p after pH adjustment.

(Drying Step 12)

At the drying step 12, the wet cake 20p after pH adjustment may be dried by using a conventionally known dryer (not shown). As a result, water is removed, and powdered clean methionine, i.e., purified methionine, is obtained.

At the drying step 12, the purified methionine may be obtained in a sufficiently water-removed state, and a method for drying the wet cake 20p is not particularly limited. The drying step 12 may be configured as in a drying step of a conventionally known production method. A drying temperature is usually 50 to 150° C., preferably 100 to 140° C. A drying time is usually 10 minutes to 24 hours, preferably 30 minutes to 2 hours. The sufficiently water-removed state means a state in which the water content of the purified methionine is 5 mass % or less.

As described above, the production method of the present invention is a method for producing purified methionine from crude methionine and, in an embodiment, usually comprises the reaction step 2, the crystallization step 4, the separation step 6, the water washing step 8, the adjustment step 10, and the drying step 12. Particularly, in the production method of this embodiment, the crude methionine wet cake 20w washed with water is obtained by a series of steps from the reaction step 2 to the water washing step 8, the pH of the wet cake 20w is adjusted at the adjustment step 10, and the wet cake 20p after pH adjustment is dried at the drying step 12. Therefore, this production method comprises (1) a step of obtaining the crude methionine wet cake 20w washed with water, (2) a step of adjusting the pH of the wet cake 20w, and (3) a step of drying the wet cake 20p after pH adjustment.

Additionally, in this production method, based on the knowledge found by the inventors in the studies on the technique capable of preventing caking of methionine, i.e., "pH of a methionine wet cake subjected to a drying treatment is deeply related to caking of methionine", the pH of the water-washed wet cake 20w is adjusted to a range of 5.2 to 6.1. In other words, the pH of the wet cake 20p after pH adjustment is 5.2 or more and 6.1 or less. The wet cake 20p after pH adjustment is subjected to the drying step. In the purified methionine obtained by this production method, caking is effectively prevented. As a result, formation of lump methionine is suppressed, so that this purified methionine is extremely favorable in handleability.

Furthermore, in this production method, whether or not caking occurs in the powdered methionine obtained by the drying step can be predicted by comprehending the pH of the methionine wet cake 20p to be subjected to the drying step. The pH adjustment of the wet cake 20p may be performed once or may be performed 2 to 5 times in a certain embodiment (pH readjustment). Since readjustment can be made in an intermediate state of a product, high-quality purified methionine can stably be produced. This production method also contributes to a reduction in manufacturing cost.

The pH of the wet cake 20p after pH adjustment is preferably 5.7 or more in that the caking of the purified methionine can more effectively be prevented. The pH of the wet cake 20p after pH adjustment is preferably 5.9 or less in that the caking of the purified methionine can further effectively be prevented. The pH of the wet cake 20p after pH adjustment is particularly preferably 5.7 or more and 5.9 or less.

In the present invention, the pH of the wet cake 20p is represented by a pH value of an aqueous solution obtained by dissolving 1.1 g of the wet cake 20p in 100 mL of water. The pH of this wet cake 20p is measured as follows. A methionine aqueous solution is prepared by dissolving 1.1 g of the wet cake 20p in 100 mL of distilled water. The temperature of this aqueous solution is adjusted to 25° C. by using a constant-temperature bath etc. While stirring the aqueous solution, a glass electrode of a glass electrode type pH meter is fixed such that a portion having a length of about 3 cm from a tip thereof is immersed in the aqueous solution. After maintaining this state for about 5 minutes and then confirming that a displayed value of a pH meter is stable, this displayed value, i.e., the pH value, is recorded. This recorded pH value is used as the pH of the wet cake 20p. For the measurement of the pH, for example, a glass electrode type pH meter manufactured by HORIBA, Ltd. is used. For the distilled water, for example, "distilled water" (trade name) manufactured by Wako Pure Chemical Industries, Ltd. is used.

As described above, at the adjusting step 10 in the embodiment of the present invention, the pH of the wet cake 20w may be adjusted by spraying the pH-adjustment water to the crude methionine wet cake 20w washed with water. From the viewpoint of effectively preventing caking of methionine, the mass of the pH-adjustment water sprayed on the wet cake 20w is preferably 50 g or more, and preferably 400 g or less, relative to the mass of 100 g of the wet cake 20w. The mass of the pH-adjustment water is more preferably 150 g or more, and more preferably 300 g or less, relative to the mass of 100 g of the wet cake 20w.

From the viewpoint of effectively preventing caking of methionine, the pH of the pH-adjustment water is preferably 2 or more, and preferably 5 or less. The pH of this pH-adjustment water is more preferably 2.6 or more, and more preferably 3.5 or less.

The pH-adjustment water used at the adjustment step 10 is not particularly limited. At this adjustment step 10, the pH-adjustment water may be an aqueous solution of an acid such as sulfuric acid or hydrochloric acid, or the pH-adjustment water may be an aqueous solution obtained by adjusting the pH of the aqueous solution containing methionine, which is used as the washing water described above, with an acid such as sulfuric acid or hydrochloric acid, i.e., an acidic aqueous solution containing methionine. From the viewpoint of preventing dissolution of methionine in the pH-adjustment water and improving the yield of methionine as a product, the pH-adjustment water is preferably an acidic aqueous solution containing methionine. In this case, the concentration of methionine contained in the pH-adjustment water is preferably 1.0 mass % or more, more preferably 2.0 mass % or more. The concentration of methionine contained in the pH-adjustment water is preferably 3.0 mass % or less.

The crude methionine wet cake 20w washed with water usually contains water. As described above, when the pH of the wet cake 20w is adjusted and the pH of the wet cake 20p obtained by the pH adjustment is within a certain range, the caking of methionine is prevented.

From the viewpoint of ensuring the purity of methionine and reducing variable costs, the water content of the wet cake 20w is preferably 40 mass % or less. The water content of the wet cake 20w in this case is obtained by a heating dry weight measurement method.

[Method for Preventing Caking of Methionine]

The above knowledge of deep relationship of the pH of the methionine wet cake to be subjected to the drying treatment with the caking of methionine is applicable to a method for preventing caking of methionine. The method for preventing caking of methionine according to the present invention will hereinafter be described.

This method for preventing caking of methionine is a method for preventing caking of methionine, and the method comprises
(1) a step of obtaining a methionine wet cake,
(2) a step of adjusting the pH of the wet cake, and
(3) a step of drying the wet cake after pH adjustment, and the pH of the wet cake after pH adjustment is 5.2 or more and 6.1 or less.

At the step of obtaining a methionine wet cake (also referred to as a wet cake formation step), a slurry containing methionine is prepared, and this slurry is separated into solid and liquid as in the solid-liquid separation of the slurry 14 in the separation step 6 described above. As a result, the methionine wet cake is obtained.

At the step of adjusting the pH of the wet cake (also referred to as an adjustment step), the pH of the wet cake is adjusted in the same manner as described for the adjustment step 10 in the production method described above. At the step of drying the wet cake after pH adjustment (also referred to as a drying step), the pH-adjusted wet cake is dried in the same manner as described for the drying step 12 in the production method described above. As a result, powdery methionine is obtained.

In this method for preventing caking, the pH of the methionine wet cake to be subjected to the drying treatment is also adjusted within a range of 5.2 to 6.1 as in the production method described above. In other words, the pH of the wet cake after pH adjustment is 5.2 or more and 6.1 or less. Therefore, in this method for preventing caking, the drying treatment is performed for the wet cake adjusted to the specific pH. Thus, the caking is effectively prevented in methionine to which this method for preventing caking is applied. As a result, the formation of lump methionine is suppressed, so that this methionine is extremely favorable in handleability.

In this method for preventing caking, the pH of the wet cake after pH adjustment is preferably 5.7 or more in that the caking of methionine can more effectively be prevented. The pH of the wet cake 20p after pH adjustment is preferably 5.9 or less in that the caking of the purified methionine can further effectively be prevented. The pH of the wet cake 20p after pH adjustment is particularly preferably 5.7 or more and 5.9 or less.

This method for preventing caking is intended for methionine that is preferably methionine from which impurities such as the alkali compounds described above are removed, i.e., purified methionine, from the viewpoint of effective prevention of caking. Therefore, by preparing a clean methionine wet cake at the wet cake forming step and performing the adjustment step and the drying step for this wet cake, caking of methionine can effectively be prevented.

This method for preventing caking is also applicable to crude methionine obtained in a production process of methionine, and in this case, preferably, this crude methionine is washed with water to remove impurities, and a clean methionine wet cake is then prepared, from the viewpoint of effective prevention of caking.

Furthermore, this method for preventing caking is also applicable to methionine stored as a product (hereinafter referred to as product methionine). In this case, if impurities are already removed from the product methionine, a slurry of this product methionine may be obtained, and this slurry may be separated into solid and liquid as in the separation step 6 described above to thereby prepare a clean methionine wet cake. If this product methionine contains impurities, preferably, the impurities are removed by washing with water and a clean methionine wet cake is then prepared, as in the case of applying the method for preventing caking of the present invention to crude methionine, from the viewpoint of effective prevention of caking.

In this way, the method for preventing caking of the present invention is applicable to methionine in various situations. Particularly, if formation of methionine lumps is confirmed in the product methionine during storage, application of this method for preventing caking enables regeneration into high-quality purified methionine through resolving caking of methionine.

As is clear from the above description, the production method of the present invention provides the purified methionine in which caking is prevented, and the application of the method for preventing caking of the present invention can prevent or eliminate the caking of methionine. Therefore, the present invention provides the method for producing purified methionine capable of preventing (or eliminating) caking of methionine and the method for preventing caking of methionine.

EXAMPLES

The present invention will hereinafter be described in more detail with examples etc.; however, the present invention is not limited only to these examples.
[Production of Powdered Methionine]

Example 1

About 1 minute was taken to put 900 mL of a crude methionine slurry into a centrifuge basket (inner diameter=100 mm, height=50 mm) rotating at 1500 revolutions per minute. The solid component of the slurry was captured with a filter cloth of the basket, and the basket was rotated at 3600 revolutions per minute for 2 minutes to shake off water, so that a crude methionine wet cake was obtained.

The mass of this wet cake was 100 g.

An aqueous solution containing 3 mass % of methionine was prepared as washing water. While rotating the basket at 400 to 500 revolutions per minute, the washing water (100 mL) was sprayed to the crude methionine wet cake by using a spray having the same structure as that of a spray 22 shown in FIG. 4 described later to wash the entire crude methionine wet cake with water. The crude methionine wet cake washed with water was thereby obtained.

Sulfuric acid was mixed with the aqueous solution containing 3 mass % of methionine to prepare pH-adjustment water (pH=2.98). This pH-adjustment water was sprayed to the wet crushed methionine wet cake washed with water described above to adjust the pH of the wet cake. As shown in Table 1, the pH of the wet cake after pH adjustment was 5.72.

In Example 1, the wet cake after pH adjustment was dried by using a vacuum dryer in a vacuum state at a temperature of 90° C. for 20 hours. The drying was followed by cooling to room temperature in the vacuum dryer to obtain powdered methionine.

Figure 4:
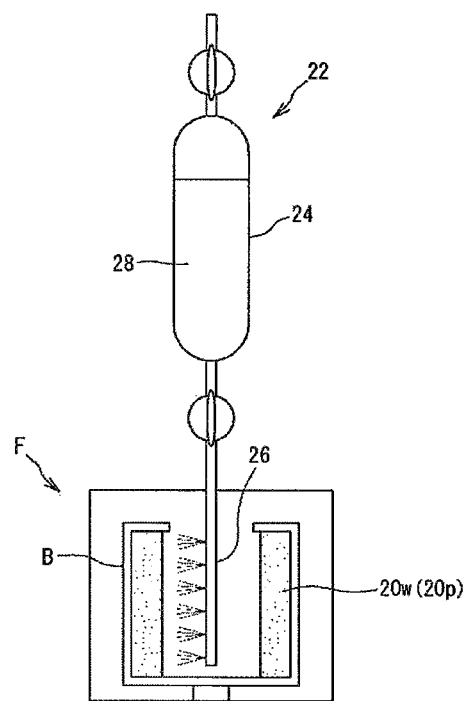
FIG. 4 is a schematic view showing a step of adjusting the pH of the wet cake in Example 1.

In Example 1, the spray 22 shown in FIG. 4 was used for spraying the pH-adjustment water. While a basket B of a centrifuge F was rotated at 400 to 500 revolutions per minute, a pH-adjustment water 28 filled in a tank 24 was sprayed from a nozzle 26 toward the wet cake 20w. The pH of the wet cake 20w was thereby adjusted. In this way, the wet cake 20p after pH adjustment was obtained.

Example 2

Powdered methionine was obtained as in Example 1 except that the amount of the washing water was 350 cc and that the pH of the pH-adjustment water was 3.2. As shown in Table 1, the pH of the wet cake after pH adjustment was 5.86 in Example 2.

Example 3

Powdered methionine was obtained as in Example 1 except that the amount of the washing water was 150 cc and that the pH of the pH-adjustment water was 3.2. As shown in Table 1, the pH of the wet cake after pH adjustment was 5.87 in Example 3.

Example 4

Powdered methionine was obtained as in Example 1 except that the amount of the washing water was 50 cc and that the pH of the pH-adjustment water was 3.2. As shown in Table 1, the pH of the wet cake after pH adjustment was 6.08 in Example 4.

Comparative Example 1

Powdered methionine was obtained as in Example 1 except that the pH of the pH-adjustment water was 2.5. As shown in Table 1, the pH of the wet cake after pH adjustment was 5.08 in Comparative Example 1.

Comparative Example 2

Powdered methionine was obtained as in Example 1 except that the amount of the washing water was 400 mL and the pH of the wet cake was not adjusted with the pH-adjustment water. In Comparative Example 2, the pH of the wet cake before drying was 6.30. In Comparative Example 2, the pH of the wet cake before drying is shown in Table 1 as the pH of the wet cake after pH adjustment.
[Evaluation of Methionine]

Into an aluminum foil vessel was put 20 g of the produced methionine. This vessel having the methionine put therein was allowed to stand for 1 hour in an atmosphere adjusted to a temperature of 50° C. and a humidity of 40% RH. After standing, the methionine was cooled until the temperature of the methionine reached room temperature. After cooling, a caking state of methionine in the vessel was evaluated. The result is shown in Table 1 below based on the following ratings:

A. almost no formation of lumps was observed;

B. formation of lumps having a size of about several mm was confirmed; and

C. formation of lumps having a size of about 10 to 20 mm was confirmed.

TABLE 1

|  | Comparative Example 1 | Example 1 | Example 2 | Example 3 | Example 4 | Comparative Example 2 |
| --- | --- | --- | --- | --- | --- | --- |
| pH | 5.08 | 5.72 | 5.86 | 5.87 | 6.08 | 6.30 |
| caking state | C | A | A | A | B | C |

As shown in Table 1, in Comparative Example 1 in which the pH of the wet cake after pH adjustment was smaller than 5.2, and in Comparative Example 2 in which the pH was larger than 6.1, formation of lumps having a size of about 10 to 20 mm was confirmed.

In contrast, in Example 1-4 in which the pH of the wet cake after pH adjustment was in the range of 5.2 to 6.1, formation of lumps having a size of only about several mm was confirmed in Example 4. Particularly, in Example 1-3 in which the pH was in the range of 5.7 to 5.9, almost no formation of lumps was recognized.

As is clear from the above result, caking of methionine is prevented in Examples as compared to Comparative Examples. The superiority of the present invention is apparent from this evaluation results.

INDUSTRIAL APPLICABILITY

The method for producing purified methionine and the method for preventing caking of methionine of the present invention provide high-quality methionine prevented from caking.

EXPLANATIONS OF LETTERS OR NUMERALS

2 reaction step
4 crystallization step
6 separation step
8 washing step
10 pH adjustment step
12 drying step
14 slurry
16 centrifuge
18 basket
20 mass (wet cake)
20w crude methionine wet cake washed with water
20p wet cake after pH adjustment
22 spray
24 tank
26 nozzle
28 pH-adjustment water

The invention claimed is:

1. A method for producing purified methionine from crude methionine, the method comprising the steps of:
   obtaining a crude methionine wet cake washed with water;
   adjusting the pH of the wet cake; and
   drying the wet cake after pH adjustment, wherein
   the pH of the wet cake after pH adjustment is 5.2 or more and 6.1 or less.

2. The method according to claim 1, wherein the pH of the wet cake after pH adjustment is 5.7 or more.

3. A method for preventing or resolving caking of methionine, the method comprising the steps of:
   obtaining a methionine wet cake;
   adjusting the pH of the wet cake; and
   drying the wet cake after pH adjustment, wherein
   the pH of the wet cake after pH adjustment is 5.2 or more and 6.1 or less.

4. The method according to claim 3, wherein the pH of the wet cake after pH adjustment is 5.7 or more.

* * * * *